US008269006B2

(12) United States Patent
Hudson et al.

(10) Patent No.: US 8,269,006 B2
(45) Date of Patent: *Sep. 18, 2012

(54) PROCESSES FOR THE SELECTIVE AMINATION OF KETOMORPHINANS

(75) Inventors: Edmund C. Hudson, Clayton, MO (US); Douglas Teramura, Valley Park, MO (US); Christopher W. Grote, Webster Groves, MO (US); Catherine E. Thomasson, Webster Groves, MO (US); Gary L. Cantrell, Troy, IL (US)

(73) Assignee: Mallinckrodt LLC, Hazelwood, MO (US)

( * ) Notice: Subject to any disclaimer, the term of this patent is extended or adjusted under 35 U.S.C. 154(b) by 446 days.

This patent is subject to a terminal disclaimer.

(21) Appl. No.: 12/586,844

(22) Filed: Sep. 29, 2009

(65) Prior Publication Data

US 2010/0081817 A1    Apr. 1, 2010

Related U.S. Application Data

(60) Provisional application No. 61/194,696, filed on Sep. 30, 2008.

(51) Int. Cl.
*C07D 489/08* (2006.01)
*C07D 489/02* (2006.01)

(52) U.S. Cl. ............................................. 546/45; 546/44

(58) Field of Classification Search .................... 546/45, 546/44
See application file for complete search history.

(56) References Cited

U.S. PATENT DOCUMENTS

| | | | |
|---|---|---|---|
| 2,772,270 A | 11/1956 | Weiss | |
| 3,717,643 A | 2/1973 | Archer | |
| 3,763,167 A | 10/1973 | Hydro | |
| 4,089,855 A | 5/1978 | Chatterjie et al. | |
| 4,443,605 A | 4/1984 | Kotick et al. | |
| 4,521,601 A | 6/1985 | Rice | |
| 4,673,679 A | 6/1987 | Aungst et al. | |
| 4,775,759 A | 10/1988 | Rice et al. | |
| 4,795,813 A | 1/1989 | Schwartz | |
| 4,912,114 A | 3/1990 | Revesz | |
| 4,991,391 A | 2/1991 | Kosinski | |
| 5,240,933 A | 8/1993 | Merz et al. | |
| 5,336,483 A | 8/1994 | de Costa et al. | |
| 5,633,259 A | 5/1997 | Qin et al. | |
| 5,668,285 A | 9/1997 | Rice et al. | |
| 5,693,820 A | 12/1997 | Helmchen et al. | |
| 5,756,745 A | 5/1998 | Kavka | |
| 5,849,915 A | 12/1998 | Kim et al. | |
| 6,184,381 B1 | 2/2001 | Ikariya et al. | |
| 6,509,467 B1 | 1/2003 | Blacker et al. | |
| 6,887,999 B1 | 5/2005 | Likhotvorik | |
| 7,045,646 B2 | 5/2006 | Tanis et al. | |
| 7,985,858 B2 * | 7/2011 | Grote et al. ...................... 546/46 |

| | | | |
|---|---|---|---|
| 2003/0194420 A1 | 10/2003 | Holl et al. | |
| 2006/0182692 A1 | 8/2006 | Fishburn et al. | |
| 2008/0045715 A1 | 2/2008 | Mitchell et al. | |

FOREIGN PATENT DOCUMENTS

| | | |
|---|---|---|
| CN | 1115318 | 1/1996 |
| CN | 1115318 A | 1/1996 |
| CN | 1939920 | 4/2007 |
| DE | 922 827 | 1/1955 |
| EP | 0 034 480 | 8/1981 |
| EP | 0 879 823 | 11/1998 |
| EP | 0 916 637 | 4/2005 |
| HU | 76478 | 9/1997 |
| WO | WO 95/32973 | 12/1995 |
| WO | WO 98/05667 | 2/1998 |
| WO | WO 03/024972 | 3/2003 |
| WO | WO 2004/085058 | 10/2004 |
| WO | WO 2005/100361 | 10/2005 |
| WO | WO 2006/008562 | 1/2006 |
| WO | WO 2006/035195 | 4/2006 |
| WO | WO 2006/052710 | 5/2006 |
| WO | WO 2007/137785 | 12/2007 |
| WO | WO 2008/137672 A1 * | 11/2008 |

OTHER PUBLICATIONS

Kirby et al., "Synthesis of 14B-Mercaptocodeine Derivatives from N-t-Butoxycarbonyl-N-northebaine", Journal of chemical Research. Miniprint., 1984, pp. 2073-2086, XP9127313.
Bentley et al., "Novel Analgesics and Molecular . . . ", Journal of the American Chemical Society, 89(13), 1967, pp. 3267-3273.
Bentley et al., "Novel Analgesics and Molecular Rearrangements in the Morphine-Thebaine Group . . . ", Journal of the American Chemical Society, 1967, 89(13), pp. 3281-3292.
Grundt et al., "Formic Acid Catalyzed Rearrangement of Thevinols . . . ", Helv. Chim. Acta, 86(7), 2003, pp. 2287-2298, XP 002560362.
Henderson et al., "Synthesis from Thebaine of 10-oxothebaine . . . ", J. Chem. Soc., 1994, (3), pp. 295-297.
Hori et al., "Synthesis of the novel Sulfur-Containing . . . ", Chemical and Pharmaceutical bulletin, 1984, 32(3), pp. 1268-1271.
Iwamura et al., "Synthesis of 6,14-ethenomorphines and the Cytostatic Activity of Tumor Cells", Gifu yakka Daigaku Kiyo, 2005, 54, pp. 45-50.
Leonard et al., "Determination of the Relative and Absolute Configuration . . . ", Organic Letters, 4(4), 2002, pp. 4201-4204, XP 002560364.
Leonard et al., "Determination of the Relative and Absolute Configuration . . . ", Organic Letters Supporting Information, 2002, XP 002563404.
Li et al., "Selective Demethylation Process in Synthesis of Etorphine and Hydrotorphine", Guanxi Daxue Xuebao, Ziran Kexueban, 2004, 29(3), pp. 265-268.
Ma, Sicai et al., "Improved Synthesis of Diprenorphine", Zhongguo Yixao Gongye Zazhi, 1992, 23(40, pp. 157-158.
Marton et al., "Herstellung von 6, 14-Ethenomorphinan-Derivaten", Monatshefte Fuer chemie, 125(11), 1994, pp. 1229-1240, XP 002560363.
Maxichen et al., "Synthesis of the Highly Efficient . . . ", Jingxi Huagong, 1996, 13(1), pp. 12-15.
Russell et al., "One-Pot synthesis Aids Scale-Up and Data Collection", Pharmaceutical Technology, Advanstar Communications, Inc. US, no. Nov. 1, 2003, pp. 17, 22, XP 002433225.

(Continued)

*Primary Examiner* — Charanjit Aulakh

(57) ABSTRACT

The present invention is generally directed to a process for the preparation of a ketomorphinan comprising maintaining a ketone group as unprotected and performing reductive amination using a hydrogen source and a catalyst.

11 Claims, No Drawings

OTHER PUBLICATIONS

Valhari et al., "Formation of 6,14-endo-ethenotetra hydrothebaine . . . ", Science International, 1992, 4(1), pp. 53-58.
Wan et al., "Synthesis of an Opiate Receptor . . . ", Shangha Dixi Yixueyuan Xuebao, 1985, 12(1), pp. 25-30.
Wang et al., "Synthesis of 3-H-thienorphine", Zhongguo Xinyao Zazhi, 2004, 13(11), pp. 1012-1015.
Woudenberg et al., "Chemistry of Opium Alkaloids . . . ", Recuell des Travaux Chimiques des Pays-Bas, 1990, 109(5), pp. 353-357.
Abdel-Magid et al., "Reductive Animation of Aldehydes and Ketones . . . ", Tetrahedron Letters, vol. 31, No. 39, 1990, p. 5395-5598.
Beyerman et al., "Synthesis of racemic and optically active codeine and morphine via the N-formylnordihydrothebainones", Journal of the Royal Netherlands Chemical Society, 97, 5, May 1978, pp. 127-130.
Beyerman et al., "Synthesis of racemic and of ( +)- and ( −)-1 methyldihydrothebainone. (Chemistry of opium alkaloids, Part IV)", Recl. Trav. Chim. Pays-Bas, 1976, 75, p. 184-188.
Bognar et al., Izvestiya po Khimiya, 1975, 81(1), p. 203-215.
Borch et al., "The cyanohydridoborate Anion as a Selective Reducing Agent", Journal of the American Chemical Society, 93:12, Jun. 16, 1971, p. 2897-2904.
Borch et al., "A New Method for the Methylation of Amines", J. Org. Chem., vol. 36, No. 10, 1972, pp. 1673-1674.
Brine et al., "Formamidinesulfinic Acid Reduction of Dihydrocodeinone Derivatives", J. Org. Chem., vol. 43, No. 8, 1978, p. 15551557.
Burke et al., "Probes for narcotic Receptor Mediated Phenomena . . . ", Heterocycles, vol. 23, No. 1, 1985, p. 99-110.
Butora et al., "Chemoenzymatic Synthesis of the Morphine Skeleton via Radical . . . ", Tetrahedron Letter's, vol. 37, No. 45, 1996, p. 8155-8158.
Campbell et al., "The Preparation of Unsymmetrical Secondary Aliphatic Amines", Jan. 1944, vol. 66, p. 82-84.
Chatterjie et al., "Reduction of 6-Ketones of the Morphine Series . . . ", J. Org. Chem., vol. 41, No. 22, 1976, p. 3624-3625.
De Costa et al., "Probes for Narcotic Receptor Mediated Phenomena . . . ", J. Med. Chem., 1992, 35, p. 2826-2835.
Farber et al., "A Synthesis of Armepavine and Related Bases. Resolution of (±)-Armepavine", Anales. Asoc. Quim. Argentina, 58, 1970, pp. 133-138.
Farber et al., "Resolution of (±)-armepavine", Chemistry and Industry, Jan. 13, 1968, pp. 57-58.
Fuiji et al., "The First Example of the Stereoselective Synthesis of . . . ", Chem. Pharm. Bull., 52(6), 2004, p. 747-750.
Fuiji et al., "Ruthenium(II)-Caatalyzed Asymmetric Transfer . . . ", J. Am. Chem. Soc., 1996, 118, p. 2521-2522.
Gao et al., "Synthesis of 7-Arylmorphinans . . . ", J. Med. Chem., 1998, 41, p. 3901-3098.
Gorlitzer et al., "Diepoxy-bis-(iminoethano)-dinaphth[2,1-b:1',2'-i]acridine[2,3+]", Arch. Pharm. (Weinheim) 325, 1992, p. 637-641.
Greene et al., "Protection for Phenols", Protective Groups in Organic Synthesis, 3rd, Ed., c1999, pp. 249-257 and 266-269.
Gribble et al., "Reactions of Sodium Borohydride in Acidic Media . . . ", Communications, Aug. 1987, p. 709-711.
Hashiguchi et al., "Asymmetric Transfer Hydrogenation of Aromatic ketones Catalyzed by chiral Ruthenium(II) Complexes", J. Am. Chem. Soc., vol. 177, No. 28, 1995, p. 7562-7563.
Huang et al., "Synthesis of (+−)-Glaucine and (+−)-Neospirodienone via an One-Pot Bischler-Napieralski Reaction and Oxidative Coupling by a Hypervalent Iodine Reagent", Helvetica chimica Acta 2004 CH, vol. 887, No. 1, 2004, pp. 167-174, XP002476119.
Kalimin et al., "Palladium-Catalyzed 2-Phenylethenylation of Codeine . . . ", Helevetica Chimca Acta, vol. 89, 2006, p. 861-869.
Kametani et al., "131. Coclaurine 7-Benzyloxy-1,2,3,4-tetrahydro-1-(p-hydroxyphenyl)-6-methoxy-2-methylisoquinoline 7-Benzyloxy-1,2,3,4-tetrahydro-1-(p-hydroxybenzyl)-6-methoxy-2-methylisoquinoline", Coclaurine, vol. 87, No. 7, 1967, pp. 757-760.
Kashdan et al., "Synthesis of 1,2,3,4-Tetrahydroisoquinolines", J. Org. Chem., 1982, 47, pp. 2638-2643.

Kitamura et al., "General Asymmetric Synthesis of Isoquinoline Alkaloids. Enantioselective Hydrogenation of Enamides Catalyzed by BINAP-Ruthenium(II) Complexes", J. Org. Chem., 1994, 59, pp. 297-310.
Koolpe et al., "Opioid Agonists and Antagonists. 6-Desoxy-6-substituted . . . ", J. Med. Chem., 1985, 28(7), p. 949-957.
Klunenberg et al., "A Remarkable Influence of the Electrolyte in Andoic cyclization of 1-Benzyltetrahydroisoquinolines to neospirodienones or Morphinandienones", Tetrahedron Letters, 1982, vol. 23, No. 44, pp. 4581-4584.
Lau et al., "Evolutiion of a Series of Non-Quinoline Leukotriene $D_4$ Receptor Antagonist . . . ", Bioorganic & Medicinal chemistry Letters, vol. 5, No. 15, 1995, p. 1615-1620.
Lazar et al., "A Selective Removal of Benzyl Protecting Groups in Arylphosphate Esters with Bromotrimethylsilane", Synthetic Communications, 22(6), 1992, p. 923-931.
Leland et al., "Analgesic narcotic antagonists. 5. 7,7-Dimethyldihydrocodeinones . . . ", J. Med. Chem.., 1981, 24, p. 717-721.
Lespagnol et al., "Preparation of amides from the homoveratrylamine and iodephenylacetic substituted acids", Chim. Therap., 1965, pp. 14-16, English Translation by FAST-TRANS.
Malspeis et al., "Metabolic Reduction of Naltrexone I. Synthesis, Separation . . . ", Res. Commun. Chem. Pathol. Pharmacol, 2(43), 1975.
Mao et al., "A Chiral Rhodium Complex for Rapid Asymmetric Transfer . . . ", Organic Letters, 1999, vol. 1, No. 6, p. 841-843.
Meuzelaar et al., "Chemistry of Opium Alkaloids, 45 Improvements in the Total Synthesis of Morphine", Eur. J. Org. Chem., 1999, pp. 2315-2321.
Nagase et al., "The Facility of Formation of a $\Delta^6$ Bond in Dihydromorphinone and Related Opiates", J. Org. Chem., 1989, 54, p. 4120-4125.
Noyori et al., "Asymmetric Catalysts by Architechtural and Functional Molecular . . . ", Agew. Chem. Int., Ed. 2001, 40, p. 40-73.
Noyori et al., "Asymmetric Transfer Hydrogenation Catalyzed by Chiral Ruthenium.Complexes", Acc. Chem. Res., 1997, 30, pp. 97-102.
Ohno et al., "Solid-Phase synthesis of 6-Sulfionylamino Morphinan Libraries", Synlett, 2002, No. 1, p. 93-96.
Olfason et al., "A New Reagent for the Selective, High-Yield N-Dealkylation of Teritary Amines: Improved Syntheses of Naltrexone and Nalbuphine", J. Org. Chem.., 1984, 49, p. 2081-2082.
Olieman et al., "Conversion of (−)-dihydrocodeinone into . . . ", Laboratory of Organic chemistry Technische Hogeschool Delft, Julianalaan 136, Delft, The Netherlands, Mar. 15, 1976.
Olsen et al., "Conjugate Addition Ligands of Opioid Antagonists . . . ", J. Med. Chem., 1990, 33(2), p. 737-741.
Palmer et al., "Asymmetric transfer hydrogenation of C=O and C=N bonds", Tetrahedron: Asymmetry 10, 1999, p. 2045-2061, XP 004174087.
Puntener et al., "New Efficient Catalysts for enantioselective Transfer Hydrogenations", Tet. Lett., 1996, 37(45), pp. 8165-8168.
Sagara et al., "Specific Affinity Labeling of . . . ", Bioorganic & Medicinal Chemistry Letters, vol. 5, No. 15, 1995, p. 1609-1614.
Saunders et al., "Assessment of relative nutritive value of proteins using streptoccus zymogenes", Chemistry and Industry, Jan. 13, 1968, pp. 56-58.
Schellenberg, "The Synthesis of Secondary and Tertiary Amines by Borohydride Reduction", Nov. 1963, p. 3259-3261.
Schmidhammer, "134. Synthesis and Biological ion of 14-Alkoxymorphinans Part [4,1]) Opioid Agonists and Partial Opioid Agonists in a Series of . . . ", Helevitca Chimca Acta, vol. 72, 1989, p. 1233-1239.
Sheth et al., "Synthesis of N-(3',4'-Dimethoxy-5'-bromophenethyl)-2-(4"-hydrioxyphenyl)-acetamide & Allied Products", Indian Journal of Chemistry, vol. 15B, Jul. 1977, pp. 595-598.
Small et al., "The Addition of Organomagnesium Halides to Pseudocodeine Types. IV. Nuclear-Substituted Morphine Derivatives", Contribution from the Cobb Chemical Laboratory, University of Virginia, Received Jun. 6, 1938, pp. 204-232.
Spadoni et al., "2-[N-Acylamino($C_1$-$C_3$)alkyl]indoles as $MT_1$ . . . ", J. Med. Chem., 1998, 41, p. 3624-3634.

Tolkachev et al., "Synthetic Investigation in [Kurarealkaloidov] Area XVI. Synthesis 1-(e'-Bromine . . . ", Organicheskoi Khimii, 1966, 36(10), pp. 1767-1772, English Translation proviced by FAST-TRANS.

Uba et al., "Stereospecific Synthesis of Codeine . . . ", Chem. Pharm. Bull., vol. 27, Issue 9, 1979, p. 2257-2258.

Uematsu et al., "Asymmetric Transfer Hydrogenation of Imines", J. Am. Chem. Soc., 1996, 118, p. 4916-4917.

Uwai et al., "Syntheses and receptor-binding studies of derivatives . . . ", Bioorganic & Medicinal Chemistry, 12, 2004, p. 417-421, XP 002488979.

H.C. van der Plas et al., "On the reaction of 2-, 3- and 4-bromo(chloro)-1,8-naphthyridine with potassium amide in liquid ammonia", Laboratory of Organic Chemistry, Agricultural University, Wagenagen, The Netherlands, (Received Oct. 10, 1977).

Van Gurp et al., "Synthesis of 7,8-Didehydro-3,4-Dimethoxy . . . ", Bull. Soc. Chim. Belg., vol. 96/n° Apr. 1987, p. 325-329.

Venkov et al., "Synthesis of isoquinolines from 2-phenylethylamines, amides, nitriles and carboxylic acids in polyphosphoric acid", Tetrahedron 19960909 GB, vol. 52, No. 37, Sep. 9, 1996, pp. 12299-12308, XP 002476120.

Voronin et al., "Synthetic Investigations in the Field of the Curare Alkaloids XII. Synthesis of Isomeric Tubocurarin Iodides", Chemistry of heterocyclic Compounds, Chemistry of Heterocyclic Compounds, 1967, pp. 447-450 (English Translation of Voronin et al., Khimiya Geterotsiklicheskikh Soedinenii, 1969, 4, pp. 606-610).

Watanabe et al., "Novel Synthesis of the Ortho Ester Derivative of 4,5-Epoxymorphinan", Organic Letters, vol. 8, No. 3, 2006, p. 523-526.

White et al., "Asymmetric Total Synthesis of (+)-Codeine via . . . ", J. Org. Chem., 1999, 64, p. 7871-7884.

White et al., "Asymmetric Synthesis of (+)-Morphine . . . ", J. Org. Chem., 1997, 62, p. 5250-5251.

Wu et al., "Asymmetric transfer hydrogenation of imines and iminiums . . . ", Chem. Commun., 2006, p. 1766-1768.

Yamakawa et al., "The Methal-Ligand Bifunctional Catalysis: A Theoretical Study on . . . ", J. Am. Chem. Soc., 2000, 122, p. 1466-1478.

* cited by examiner

PROCESSES FOR THE SELECTIVE AMINATION OF KETOMORPHINANS

CROSS REFERENCE TO RELATED APPLICATIONS

This application claims priority from U.S. Provisional Application No. 61/194,696, filed on Sep. 30, 2008, which is hereby incorporated by reference in its entirety.

FIELD OF THE INVENTION

The present invention generally relates to processes for the synthesis of intermediates or end product ketomorphinans.

BACKGROUND OF THE INVENTION

N-alkylated ketomorphinans are important pharmaceuticals, typically used as analgesics, opiate agonists, and antagonists. With the increasing use of these agents, a practical and effective method of preparation of these compounds is vital to synthesizing diverse N-alkyl substituted ketomorphinans.

N-alkylated ketomorphinans may be prepared using a reductive alkylation reaction. In this type of reaction, the free base of the amine is reacted with an aldehyde forming an imine, iminium salt, or Schiff Base. Reduction of the Schiff Base is normally accomplished by the use of a hydride transfer agent. Previous reductive alkylation methodologies, however, require that the ketone be protected prior to reduction of the imine and then de-protected after reductive amination to restore the ketone group.

Conventional reducing reagents for reductive alkylation may include borohydride reagents (e.g., sodium borohydride reagents, sodium cyanoborohydride), boranes, and aluminum hydride reagents (e.g., lithium aluminum hydride). See, for example, A. F. Abdel-Magid, et al., *Reductive Amination of Aldehydes and Ketones by Using Sodium Triacetoxyborohydride*, Tet. Lett. 31 (39), pp. 5595-98 (1990). These reagents typically need to be used in stoichiometric quantities to achieve complete reduction. Difficulties resulting from this synthetic method include the release of boron or aluminum salts from the product. Improved reductive alkylation procedures have utilized metal catalytic methodology to achieve the reduction. See, for example, WO 2006/035195 (N. Goodwin, et al.). Hydrogen gas in the presence of a transition metal catalyst has also been used to achieve this reduction. Yet even in the most recent methodologies, if carbonyl compounds are present and not protected, the carbonyls have been reduced to alcohols. By way of example, the use of a Noyori catalyst (ruthenium bound by an activating ligand) along with a hydrogen source reduces a 6-keto group to the corresponding alpha-hydroxy-epimer.

Thus, a need remains for a quick and effective synthetic method for the preparation of N-alkylated ketomorphinans resulting in high yields. In particular, a need remains for a process for the preparation of an N-alkylated ketomorphinan while maintaining the ketone group as unprotected. A need also remains for a process for the preparation of an N-alkylated ketomorphinan while maintaining the ketone group as unprotected, wherein the ketone functionality within the ketomorphinan is not substantially reduced.

SUMMARY OF THE INVENTION

Among the various aspects of the present invention is a process for the preparation of N-alkylated ketomorphinans. The process of the present invention may comprise maintaining a ketone group of an N-imine ketomorphinan or hemiaminal ketomorphinan, and reducing the N-imine moiety or a hemiaminal moiety in the presence of a hydrogen source and a catalyst. Generally, the N-imine ketomorphinan or hemiaminal ketomorphinan may comprise an iminium salt. In one preferred aspect, the N-imine ketomorphinan or hemiaminal ketomorphinan is formed by reacting a 6-ketonormorphinan with an aldehyde.

Briefly, therefore, one aspect of the present invention is directed to a process for the preparation of a N-alkylated ketomorphinan comprising Formula (IV):

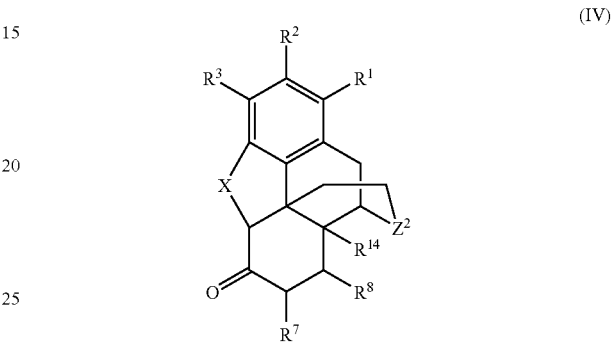

the process comprising: maintaining a ketone group of a N-imine ketomorphinan or hemiaminal ketomorphinan as unprotected; and, reducing the N-imine ketomorphinan or hemiaminal ketomorphinan in the presence of a hydrogen source and a catalyst without substantially reducing the 6-keto functionality to an alcohol, the N-imine ketomorphinan or hemiaminal ketomorphinan comprising Formula (III):

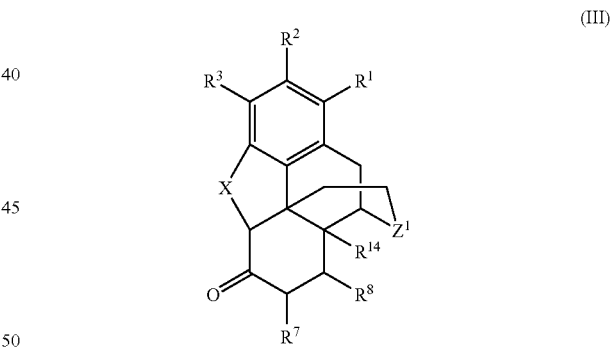

wherein:

$R^1$, and $R^2$ are independently selected from the group consisting of hydrogen, hydrocarbyl, substituted hydrocarbyl, halo, and $\{-\}OR^{15}$;

$R^3$, $R^7$, and $R^8$ are independently selected from the group consisting of hydrogen, hydrocarbyl, substituted hydrocarbyl, and $\{-\}OR^{15}$;

$R^9$ is selected from the group consisting of hydrogen, acyl, hydrocarbyl, substituted hydrocarbyl, and heterocyclo;

$R^{14}$ is selected from the group consisting of hydrogen and hydroxy;

$R^{18}$ is selected from the group consisting of hydrogen, hydrocarbyl, substituted hydrocarbyl, and a hydroxy protecting group;

X is a heteroatom;

$Z^1$ is selected from the group consisting of {—}NCH(OH)($R^9$), and {—}$N^+$=CH($R^9$); and, $Z^2$ is {—}$NCH_2R^9$ In another embodiment, the present invention is also directed to a process for the preparation of a N-alkylated ketomorphinan comprising Formula (II):

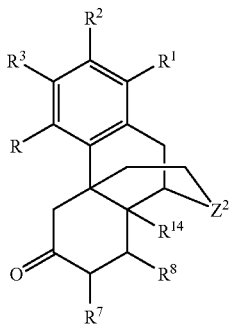

(II)

the process comprising:

maintaining a ketone group of a N-imine ketomorphinan or hemiaminal ketomorphinan as unprotected; and, reducing the N-imine ketomorphinan or hemiaminal ketomorphinan in the presence of a hydrogen source and a catalyst without substantially reducing the 6-keto functionality to an alcohol, the N-imine ketomorphinan or hemiaminal ketomorphinan comprising Formula (I):

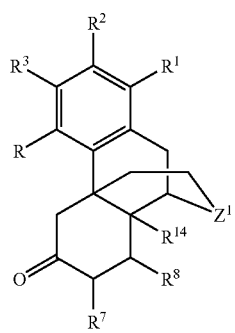

(I)

wherein:

R, $R^1$, and $R^2$ are independently selected from the group consisting of hydrogen, hydrocarbyl, substituted hydrocarbyl, halo, and {—}$OR^{15}$;

$R^3$, $R^7$, and $R^8$ are independently selected from the group consisting of hydrogen, hydrocarbyl, substituted hydrocarbyl, and {—}$OR^{15}$;

$R^9$ is selected from the group consisting of hydrogen, acyl, hydrocarbyl, substituted hydrocarbyl, and heterocyclo;

$R^{14}$ is selected from the group consisting of hydrogen and hydroxy;

$R^{15}$ is selected from the group consisting of hydrogen, hydrocarbyl, substituted hydrocarbyl, and a hydroxy protecting group;

$Z^1$ is selected from the group consisting of {—}NCH(OH)($R^9$), and {—}$N^+$=CH($R^9$);

$Z^2$ is {—}$NCH_2R^9$.

Other aspects and features will be in part apparent and in part pointed out hereinafter.

DETAILED DESCRIPTION OF THE INVENTION

The present invention is directed to improved synthetic methods for the preparation of N-alkylated ketomorphinans, salts, intermediates, and analogs thereof. In one aspect of the present invention, the synthetic methods involve maintaining a ketone group as unprotected and utilizing a catalyst and a hydrogen source to reduce an N-imine moiety or a hemiaminal moiety of a ketomorphinan (sometimes collectively referred to herein as the "N-imine/hemiaminal ketomorphinan") to the corresponding alkyl group. Without being limited by theory, the present invention includes a process for the preparation of an N-alkylated ketomorphinan by selective catalytic hydrogen transfer reduction of the iminium salt formed from the reaction of the ketonormorphinan and an aldehyde (e.g., a hydrocarboxaldehyde). The reductive amination reaction of the present invention may be referred to as selective because it reduces the N-imine ketomorphinan or hemiaminal ketomorphinan without substantially reducing the ketone functionality, even though the ketone group is maintained as unprotected. Previous methodologies would require the ketone group to be protected prior to reduction of the imine and then de-protected after reductive amination to restore the ketone group, otherwise the ketone group would be substantially reduced to an alcohol. In accordance with another aspect of the present invention, ketone groups within the ketomorphinan are not substantially reduced to alcohols as would have been previously expected. In another aspect, the present invention does not utilize or require an adjunct metal ligand (i.e. an activating ligand as required by a Noyori catalyst). Yet another surprising aspect of the present invention is that certain non-activating ligands, including ethanolamine, have been discovered to be ineffective at reducing the ketone group and may be combined with the hydrogen source and catalyst. Thus, the processes of the present invention may provide faster and more effective synthetic methods for the preparation of N-alkylated ketomorphinans. The resulting N-alkylated ketomorphinan may further be derivatized, if desired, in one or more additional steps to form other morphinans.

As an overview, an exemplary process for the preparation of N-alkylated ketomorphinan may optionally proceed via a two-step synthetic route. In the first step, a 6-norketomorphinan (e.g., "nor" meaning no R group on the nitrogen) may be reacted with an aldehyde to form an N-imine ketomorphinan or hemiaminal ketomorphinan. In the next step, the N-imine ketomorphinan or hemiaminal ketomorphinan may be reduced to form the N-alkylated ketomorphinan without substantially reducing the 6-keto functionality to an alcohol. In one iteration, any nor-opioid may be used instead of the 6-ketonormorphinan. In one exemplary iteration, the two-step synthetic route proceeds in accordance with Reaction Scheme 1:

Reaction Scheme 1
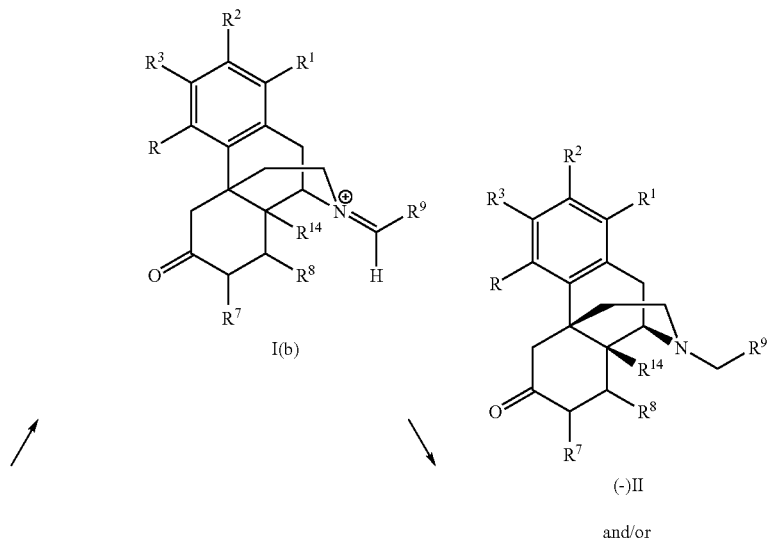
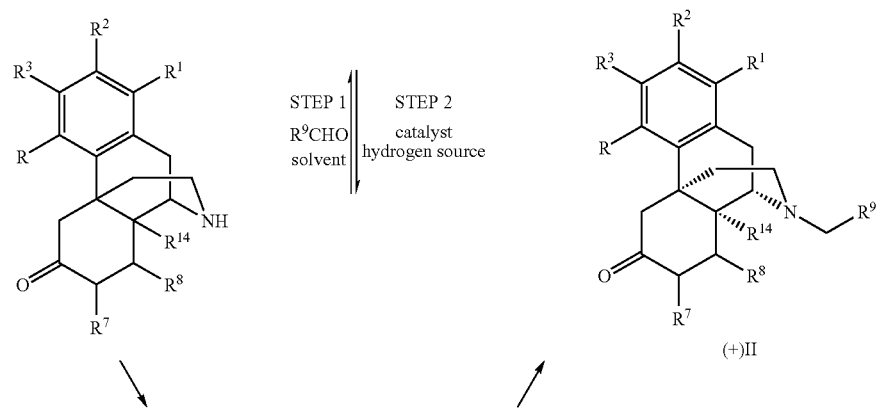
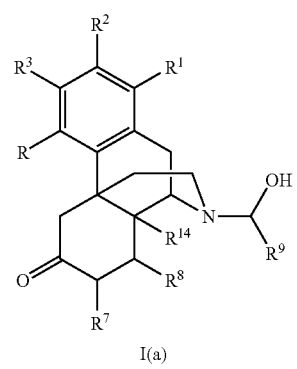

Referring to Reaction Scheme I, the compound comprising Formula (Ia) or (Ib) comprises N-imine ketomorphinan or hemiaminal ketomorphinan, respectively, and the compound comprising Formula (II) comprises an N-alkylated ketomorphinans formed according to one non-limiting iteration of the invention. Each of the R groups is described in more detail below.

In yet another exemplary iteration, the two-step synthetic route proceeds in accordance with Reaction Scheme 2:

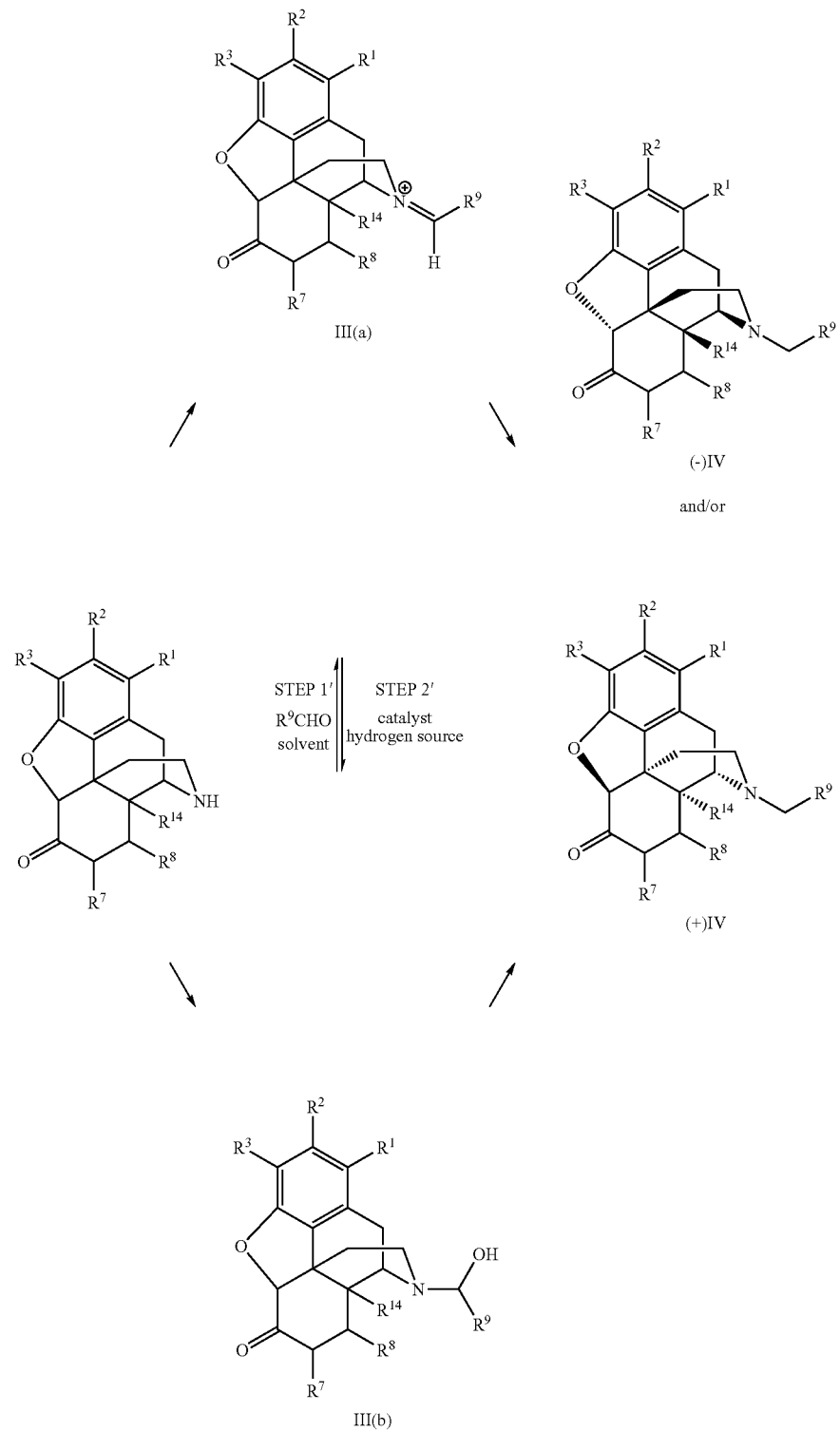

Referring to Reaction Scheme 2, the compound comprising Formula (IIIa) or (IIIb) comprises N-imine ketomorphinan or hemiaminal ketomorphinan, respectively, and the compound comprising Formula (IV) comprises an N-alkylated ketomorphinan formed according to an additional non-limiting iteration of the invention. Each of the R groups is described in more detail below.

For purposes of discussion, the ring atoms of the ketomorphinans of the present invention are numbered and illustrated as follows. The below illustrated numbered ketomorphinan, wherein an oxygen atom, C-4, and C-5 comprise an ether group, is not intended to be limiting.

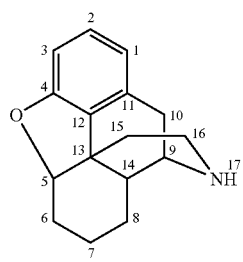

(I) Step A: Formation of the N-imine or N-hemiaminal Ketomorphinan

Optionally, as depicted in Reaction Schemes 1 and 2, the N-imine ketomorphinan or hemiaminal ketomorphinan may be formed by reacting an aldehyde comprising the formula $R^9CHO$ with a ketonormorphinan. In one embodiment according to Reaction Scheme 1, the ketonormorphinan comprises the Formula (A):

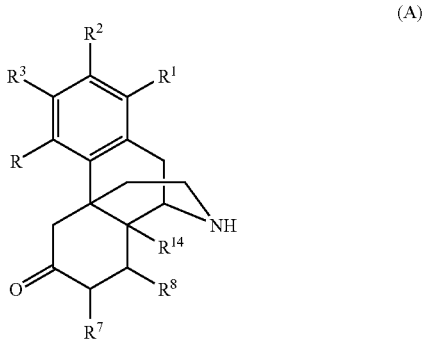

wherein:
R, $R^1$, and $R^2$ are independently selected from the group consisting of hydrogen, hydrocarbyl, substituted hydrocarbyl, halo, and {—}$OR^{15}$;
$R^3$, $R^7$, and $R^8$ are independently selected from the group consisting of hydrogen, hydrocarbyl, substituted hydrocarbyl, and {—}$OR^{15}$;
$R^9$ is selected from the group consisting of hydrogen, acyl, hydrocarbyl, substituted hydrocarbyl, and heterocyclo;
$R^{14}$ is selected from the group consisting of hydrogen and hydroxy; and
$R^{15}$ is selected from the group consisting of hydrogen, hydrocarbyl, substituted hydrocarbyl, and a hydroxy protecting group.

In another embodiment according to Reaction Scheme 2, the ketonormorphinan comprises the Formula (B):

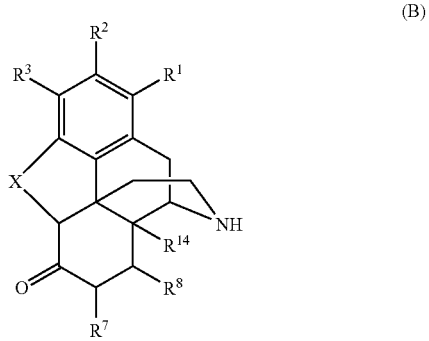

wherein:
$R^1$, $R^2$, $R^3$, $R^7$, $R^8$, $R^9$, $R^{14}$, and $R^{15}$ are as previously defined for compounds comprising Formula (A); and
X is a heteroatom. In an exemplary embodiment, the heteroatom is oxygen.

In step A, the reaction commences by contacting either the compound of Formula (A) or (B) with an aldehyde comprising $R^9CHO$ in the presence of a solvent. For iterations of the invention where an N-alkylated ketomorphinan comprising Formula (II) is desired, then compound (A) is contacted with the aldehyde. Alternatively, for iterations of the invention where an N-alkylated ketomorphinan comprising Formula (IV) is desired, then compound (B) is contacted with the aldehyde.

The aldehyde, as stated above, comprises $R^9CHO$, wherein $R^9$ is selected from the group consisting of hydrogen, acyl, hydrocarbyl, substituted hydrocarbyl, and heterocyclo. In one embodiment, $R^9$ is a hydrocarbyl or a substituted hydrocarbyl. In one exemplary embodiment, the aldehyde is a hydrocarboxaldehyde. In another embodiment, the aldehyde is a substituted acetaldehyde (e.g., heterocyclic substitution). In yet another embodiment, the aldehyde is a substituted acetaldehyde comprising a long alkyl chain. Exemplary hydrocarboxaldehydes include formaldehyde, acetaldehyde, cyclopropanealdehyde, cyclobutaneadehyde, benzaldehyde, substituted benzaldehyde, and combinations thereof. The aldehyde is typically introduced in an amount ranging from about 1.0 to about 3.0 equivalents of aldehyde per equivalent of ketomorphinan having Formula (A) or (B), and more preferably in an amount ranging from about 1.0 to about 2.0 equivalents.

As will be appreciated by a skilled artisan, the choice of solvents can and will vary without departing from the scope of the invention. Generally, the solvent will be comprised of an organic solvent. Representative organic solvents include, but are not limited to, alkane and substituted alkane solvents (including cycloalkanes), aromatic hydrocarbons, esters, ethers, ketones, combinations thereof, and the like. Specific organic solvents that may be employed, include, for example, acetonitrile, benzene, butyl acetate, t-butyl methylether, t-butyl methylketone, chlorobenzene, chloroform, chloromethane, cyclohexane, dichloromethane, dichloroethane, diethyl ether, ethyl acetate, fluorobenzene, heptane, hexanes, isobutylmethylketone, isopropyl acetate, methylethylketone, methyltetrahydrofuran, pentyl acetate, n-propyl acetate, tetrahydrofuran, toluene, isopropanol, n-propanol, ethanol, n-butanol, combinations thereof, and the like. In an exemplary embodiment, the organic solvent may be selected from the group consisting of methanol, acetonitrile, toluene, ethyl acetate or a combination thereof.

In general, the reaction may be conducted at a temperature that ranges from about 10° C. to about 85° C. for a period of time that is sufficient to convert a substantial portion of the compound comprising Formula (A) or (B) to the compound comprising Formula (I) or (III), respectively. In one example, when isopropanol is used as a solvent, reflux may be preferred at about 82° C. In a preferred embodiment, the temperature of the reaction may range from about 10° C. to about 60° C. As understood by one of skill in the art, reaction temperatures will vary depending on the solvent and aldehyde being used. In addition, the reaction may be preferably performed under ambient pressure, and preferably in an inert atmosphere (e.g., nitrogen or argon).

Typically, the reaction is allowed to proceed for a sufficient period of time until the reaction is complete, as determined by chromatography (e.g., HPLC). In this context, a "completed reaction" generally means that the reaction mixture contains a significantly diminished amount of compounds comprising either Formula (A) or (B) and a significantly increased amount of compounds comprising Formula (I) or (III) compared to the amounts of each present at the beginning of the reaction. The reaction, for example, may be carried out at about room temperature (25° C.) over a period of about 1 to about 5 hours, typically about 3 hours. In an alternative embodiment, the reaction may take from about 1 to about 7 days. Whether more or less reaction time is required may be based on HPLC analysis of the reaction mixture. An azeotropic distillation step may be added to increase the reaction rate of imine formation. After the reaction is completed, the product (i.e., the compound comprising Formula (I) or (III)) may be isolated by methods generally known in the art.

(II) Step B: Formation of the N-alkylated Ketomorphinan

In Step B, the N-imine ketomorphinan or hemiaminal ketomorphinan is reduced to form the N-alkylated ketomorphinan without substantially reducing the 6-keto functionality to an alcohol. It is envisioned that the N-imine ketomorphinan or hemiaminal ketomorphinan may be formed by either the process detailed in Step A, or by other methods generally known in the art. Either way, the N-imine ketomorphinan or hemiaminal ketomorphinan is typically contacted with a catalyst and a hydrogen source to form the N-alkylated ketomorphinan.

(a) N-Alkylated Ketomorphinan Comprising Formula (II)

In one embodiment, the N-alkylated ketomorphinan may comprise Formula (II) in accordance with one iteration of Reaction Scheme 1. As depicted in Reaction Scheme 1, to form a compound of Formula (II) a compound comprising Formula (I) is contacted with a catalyst and a hydrogen source. The N-imine and the hemiaminal moieties of Formula (I) for this embodiment comprise:

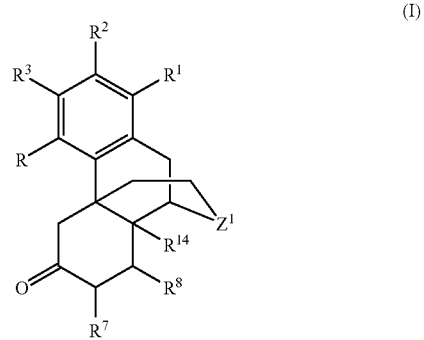

wherein:
R, $R^1$, and $R^2$ are independently selected from the group consisting of hydrogen, hydrocarbyl, substituted hydrocarbyl, halo, and $\{-\}OR^{15}$;
$R^3$, $R^7$, and $R^8$ are independently selected from the group consisting of hydrogen, hydrocarbyl, substituted hydrocarbyl, and $\{-\}OR^{15}$;
$R^9$ is selected from the group consisting of hydrogen, acyl, hydrocarbyl, substituted hydrocarbyl, and heterocyclo;
$R^{14}$ is selected from the group consisting of hydrogen and hydroxy;
$R^{15}$ is selected from the group consisting of hydrogen, hydrocarbyl, substituted hydrocarbyl, and a hydroxy protecting group; and
$Z^1$ is selected from the group consisting of $\{-\}NCH(OH)(R^9)$, and $\{-\}N^+=CH(R^9)$.

In one embodiment for compounds comprising Formula (I), $Z^1$ is $>NCH(OH)(R^9)$ or $>N^+=CH(R^9)$, $R^3$ is typically $-OR^{15}$ where $R^{15}$ is hydrogen, alkyl, acyl, alkaryl, aryl, or a hydroxy protecting group. In one example of this embodiment, $R^{15}$ is hydrogen, $C_{1-8}$ alkyl, aryl, $C_{1-8}$alkyl-C(O)—, aryl-C(O)—, $C_{1-8}$ alkyl-OC(O)—, or aryl-OC(O)—. In another example, $R^{15}$ is hydrogen or $C_{1-8}$ alkyl; preferably hydrogen or methyl. In a preferred example, $R^{15}$ is hydrogen.

In an additional embodiment for compound comprising Formula (I), $R^1$, $R^2$, $R^7$, and $R^8$ are hydrogen. In an alternative embodiment, at least one of $R^1$, $R^2$, $R^7$, and $R^8$ is other than hydrogen; for example, $R^1$ may be hydrocarbyl, halo, or $\{-\}OR^{15}$ where $R^{15}$ is hydrogen, alkyl, acyl, alkaryl, aryl, or a hydroxy protecting group. In another example, $R^7$ is a substituted hydrocarbyl group; for example, 3,3-dimethylbutan-2-ol.

The N-alkylated ketomorphinan according to this embodiment comprises Formula (II):

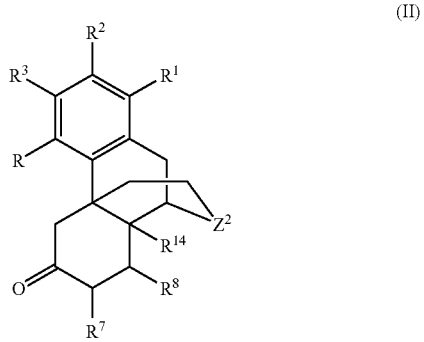

wherein:
R, $R^1$, $R^2$, $R^3$, $R^7$, $R^8$, $R^9$, $R^{14}$, and $R^{15}$ are as previously defined for compounds comprising Formula (I); and
$Z^2$ is {—}$NCH_2R^9$.

(b) N-Alkylated Ketomorphinan Comprising Formula (IV)

In one embodiment, the N-alkylated ketomorphinan may comprise Formula (IV) in accordance one iteration of Reaction Scheme 2. As depicted in Reaction Scheme 2, to form a compound of Formula (IV) a compound comprising Formula (III) is contacted with a catalyst and a hydrogen source. The N-imine and the hemiaminal moieties of Formula (III) for this embodiment comprise:

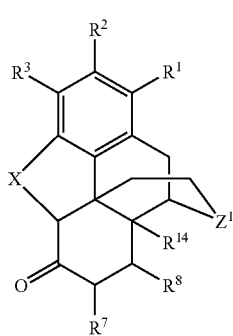

(III)

wherein:
$R^1$, $R^2$, $R^3$, $R^7$, $R^8$, $R^9$, $R^{14}$, and $R^{15}$; and $Z^1$ is are as previously defined for compounds comprising Formula (I); and
X is a heteroatom.

In one embodiment for compounds comprising Formula (III), $Z^1$ is >NCH(OH)($R^9$) or >$N^+$=CH($R^9$), $R^3$ is typically —$OR^{15}$ where $R^{15}$ is hydrogen, alkyl, acyl, alkaryl, aryl, or a hydroxy protecting group. In one example of this embodiment, $R^{15}$ is hydrogen, $C_{1-8}$ alkyl, aryl, $C_{1-8}$alkyl-C(O)—, aryl-C(O)—, $C_{1-8}$ alkyl-OC(O)—, or aryl-OC(O)—. In another example, $R^{15}$ is hydrogen or $C_{1-8}$ alkyl; preferably hydrogen or methyl. In a preferred example, $R^{15}$ is hydrogen.

In an additional embodiment for compound comprising Formula (III), $R^1$, $R^2$, $R^7$, and $R^8$ are hydrogen. In an alternative embodiment, at least one of $R^1$, $R^2$, $R^7$, and $R^8$ is other than hydrogen; for example, $R^1$ may be hydrocarbyl, halo, or {—}$OR^{15}$ where $R^{15}$ is hydrogen, alkyl, acyl, alkaryl, aryl, or a hydroxy protecting group. In another example, $R^7$ is a substituted hydrocarbyl group; for example, 3,3-dimethylbutan-2-ol.

The N-alkylated ketomorphinan according to this embodiment comprises Formula (IV):

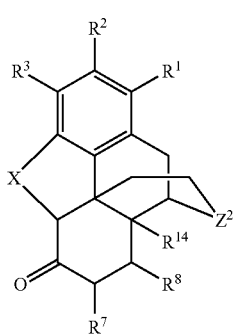

(IV)

wherein:
$R^1$, $R^2$, $R^3$, $R^7$, $R^8$, $R^9$, $R^{14}$, and $R^{15}$; and X are as previously defined for compounds comprising Formula (III); and
$Z^2$ is {—}$NCH_2R^9$.

In one embodiment of the present invention, the ketomorphinan may correspond to Formula (IV) or (II), where $R^9$ is hydrogen, or substituted or unsubstituted $C_{1-8}$ alkyl, $C_{2-8}$ alkenyl, aryl, heterocyclo or acyl. Typical acyl groups include, but are not limited to, esters, amides, and carbamates. In another embodiment, $R^9$ is hydrogen, methyl, ethyl, propyl, cyclopropyl, cyclopropylmethyl, butyl, isobutyl, t-butyl, cyclobutyl, cyclobutylmethyl, phenyl, methylcarbonyl, ethylcarbonyl, propylcarbonyl, cyclopropylcarbonyl, butylcarbonyl, isobutylcarbonyl, cyclobutylcarbonyl, or allyl; preferably, hydrogen, methyl, ethyl, phenyl, cyclopropyl or cyclobutyl. In one preferred example, $R^9$ is cyclopropyl. In another preferred example, $R^9$ is cyclobutyl. In each of the foregoing embodiments, X is preferably oxygen.

Exemplary ketomorphinan products made according to the processes of the present invention may include nalbuphone, naltrexone, naloxone, and combinations thereof. Generally, nalbuphone may be alternatively referred to as 6-ketonalbuphine.

(c) Reaction Mixture

Step 2 of either Reaction Scheme 1 or Reaction Scheme 2 generally commences by contacting a compound comprising Formula (I) or (III) with a catalyst and a hydrogen source. Suitable compounds comprising Formula (I) and (III) are detailed in Sections (Ia) and (Ib), respectively. Typically, for this type of reaction, the N-imine ketomorphinan and the hemiaminal ketomorphinan (e.g., compound (I) or (III)) are in equilibrium. Notably, the ketone functional group at C-6 is maintained as unprotected during the reductive reaction. When treated with a hydrogen source and a catalyst (e.g., ruthenium, rhodium, or iridium), as described herein, the N-imine moiety is selectively converted to the corresponding tertiary amino group and the hydroxy group of the hemiaminal moiety is removed thereby forming the N-alkylated ketomorphinan product (i.e., compound (II) or (IV)). Despite the reduction to the imine and hemiaminal moieties, the ketone functional group is not substantially reduced (e.g., reduced less than about 40-50%, more preferably less than about 30-40%, more preferably less than about 15-30%, more preferably less than about 10-15%, more preferably less than about 5-10%, and even more preferably less than about 3-5%).

Generally speaking, a suitable catalyst will facilitate reductions of the hemiaminal ($Z^1$=>NCH(OH)($R^9$)) and/or the imine ($Z^1$=>$N^+$=CH($R^9$)) moieties without reducing the keto functional group to an alcohol, such as the 6-keto functional group of the compound comprising Formula (I) or (III). These catalysts may comprise a metal source consisting of a ruthenium complex, a rhodium complex, an iridium complex, or a combination thereof. The catalyst may be a ruthenium complex or a rhodium complex. In another example, the catalyst comprises a dichloro(arene)Ru(II) dimer, dichloro(pentamethylcyclopentadienyl)Rh(II) dimer, BINAP-Ru (II) diacetate, BINAP-Ru (II) dichloride, BINAP-Ru (II) dibromide, BINAP-Ru (II) diiodide, [RuCl((R or S)BINAP) ($C_6H_6$)]Cl, dichloro(pentamethylcyclopentadienyl)iridium (III) dimer, Ru(III) chloride, $RuCl_3$ hydrate, Ru(III) acetylacetonate, tetraalkylammonium $RuCl_4$, or pyridinium $RuCl_4$. In yet another aspect, the present invention does not utilize or require a metal adjunct activating ligand. See, e.g., WO 2007/137785 to Grote, et al. reciting common Noyori activating ligands including (1S,2S)-(+)-N-4-toluenesulfonyl-1,2- diphenylethylene-1,2-diamine,(1R,2R)-(−)-N-4-toluene-sulfonyl-1,2-diphenylethylene-1,2-diamine,dl-N-tosyl-1,2-diphenylethylenediamine, N-tosyl-1,2-diphenylethylenediamine,N-tosyl-1,2-ethylenediamine, and N-tosyl-1,2-diaminocyclohexane. In particular, Noyori activating ligands may undesirably reduce the 6-keto group to the corresponding alpha-hydroxy-epimer. Another aspect of the present invention is that certain non-activating ligands, including ethanolamine, have surprisingly been discovered to be ineffective at reducing the 6-keto group and may be combined with the hydrogen source and catalyst of the present invention.

The hydrogen source may include any such source known to those skilled in the art. Methods of hydrogenation include in situ hydrogen transfer and high-pressure hydrogenation. In one example, the hydrogen source is hydrogen gas. An alternative to hydrogen gas is producing hydrogen in situ through hydrogen transfer methods. In an exemplary embodiment, the hydrogen source is a protic compound. In a more restrictive embodiment, the protic compound may be selected from the group consisting of formic acid, organic or inorganic salts of formic acid, isopropanol, n-propanol, n-butanol, and a combination thereof. In other embodiments, triethylamine may be used. The hydrogen source may also comprise an organic or inorganic salt of formic acid, preferably, the triethylamine salt of formic acid. By way of non-limiting example, the hydrogen source may be about a 5:2 mixture of formic acid to triethylamine. In the non-limiting example, the reaction mixture of about 5:2 of formic acid to triethylamine is not maintained.

The molar ratio of the N-imine ketomorphinan and the hemiaminal ketomorphinan to the catalyst to the hydrogen source (i.e., hydrogen donor) may vary without departing from the scope of the invention. In one embodiment, the molar ratio of N-imine ketomorphinan and the hemiaminal ketomorphinan to the catalyst to the hydrogen source may range from about 1:0.0001:1 to about 1:0.1:20. In an exemplary embodiment, the molar ratio of N-imine ketomorphinan and the hemiaminal ketomorphinan to the catalyst to the hydrogen source may range from about 1:0.005:2 to about 1:0.05:12. In a preferred embodiment, the relative proportion of isopropanol to N-imine ketomorphinan and hemiaminal ketomorphinan may be from about 1 equivalent to large excess. Generally, the hydrogen donor may comprise formic acid or a formic acid salt.

The reaction is typically conducted in the presence of a solvent. The solvent may be an organic solvent such as the organic solvents detailed in Section (I). In an alternative embodiment, the solvent may be a nitrile (e.g., acetonitrile, propionitrile), tetrahydrofuran (THF), an alcohol (e.g., methanol, ethanol, etc.), a halocarbon (e.g., a chloroalkyl such as dichloromethane, chloroform, 1,2-dichloroethane, or tetrachloroethylene), dimethylformamide (DMF), dimethylacetamide (DMAc), N-methylpyrrolidinone (NMP), an alkyl acetate (e.g., ethyl acetate or propyl acetate), toluene, water, or a combination thereof. In yet another example, the solvent may be acetonitrile, DMAc or a combination of acetonitrile and methanol. The substrate to solvent ratio is from about 1:2 to about 1:20, preferably about 1:4 to about 1:5.

The reaction can be conducted at a temperature range from ambient temperature (~20° C.) to about 120° C. In one example, the reaction is carried out at temperature range of about 0° C. to about 100° C., preferably from about room temperature (~20° C.) to about 60° C. Typically, the reaction is allowed to proceed for a sufficient period of time until the reaction is complete, as determined by chromatography (e.g., HPLC).

The yield of the N-alkylated ketomorphinan may vary. Typically, the yield of the N-alkylated ketomorphinan may range from about 50% to about 99%. In one embodiment, the yield of the N-alkylated ketomorphinan may range from about 70% to about 80%. In another embodiment, the yield of the N-alkylated ketomorphinan may range from about 80% to about 90%. In a further embodiment, the yield of the N-alkylated ketomorphinan may be greater than 90%.

The compounds comprising any of Formulas (I), (II), (III) or (IV) or any of the intermediates detailed herein may have a (−) or (+) stereochemistry configuration with respect to the rotation of polarized light. More specifically, each chiral center may have an R or an S configuration. The number of chiral centers can and will vary depending on the compound.

Some compounds described herein, such as compounds comprising Formula (I) or (II), may have three chiral centers, namely carbons 13, 14, and 9 (C13, C14, and C9). For these compounds, the stereochemistry for C13, C14, and C9 may be selected from the group consisting of RRR, RSR, RRS, RSS, SRR, SSR, SRS, and SSS. In this iteration, C15 and C16 carbons are both either on the alpha face of the molecule or the beta face of the molecule.

Alternatively, other compounds described herein, such as compounds comprising Formula (III) or (IV), may have four chiral centers, namely C-5, C-13, C-14, and C-9. For these compounds, the stereochemistry for C-5, C-13, C-14, and C-9 may be selected from the group consisting of RRRR, RRSR, RRRS, RRSS, RSRR, RSSR, RSRS, RSSS, SRRR, SRSR, SRRS, SRSS, SSRR, SSSR, SSRS, and SSSS. In this iteration, C15 and C16 carbons are both either on the alpha face of the molecule or the beta face of the molecule.

The invention also encompasses use of pharmaceutically acceptable salts of any of the compounds described herein. Pharmaceutically acceptable cations include metallic ions and organic ions. More preferred metallic ions include, but are not limited to appropriate alkali metal salts, alkaline earth metal salts and other physiologically acceptable metal ions. Exemplary ions include aluminum, calcium, lithium, magnesium, potassium, sodium and zinc in their usual valences. Preferred organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N methylglucamine) and procaine. Exemplary pharmaceutically acceptable acids include without limitation hydrochloric acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid, oxalacetic acid, fumaric acid, propionic acid, aspartic acid, glutamic acid, benzoic acid, and the like.

In yet another iteration, the processes of the present invention may also be effective on morphinans not having a 6-keto group. In such an embodiment, the processes of the present invention may be effective at performing an imine reduction. As such, in one iteration, the present invention may be a process for the preparation of an N-alkylated morphinan, the process comprising contacting a morphinan comprising an imine moiety or a morphinan comprising a hemiaminal moiety with a catalyst and a hydrogen source in a manner such that the imine moiety or hemiaminal moiety is reduced to form the N-alkylated morphinan. In yet another iteration, the present invention may be a process for the preparation of an N-alkylated morphinan, the process comprising contacting a morphinan comprising an imine moiety or a morphinan comprising a hemiaminal moiety with a non-activated catalyst (e.g., non-activated Noyori catalyst) and a hydrogen source in a manner such that the imine moiety or hemiaminal moiety is reduced to form the N-alkylated morphinan. The N-imine morphinan or hemiaminal morphinan may be formed by reacting an aldehyde comprising the formula $R^9CHO$ with a normorphinan. The aldehyde may be selected from the group consisting of formaldehyde, acetaldehyde, cyclopropanecarboxaldehyde, cyclobutanecarboxaldehyde, benzaldehyde, substituted benzaldehyde, and a combination thereof. In addition, the amount of aldehyde may be from about 1.0 to about 3.0 equivalents per equivalent of the normorphinan. The reaction of the aldehyde and the normorphinan may occur within a temperature range from about 0° C. to about 100° C.

Definitions

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

As used herein, the symbol ">" is used in conjunction with the imine nitrogen atom and the hemiaminal nitrogen atom to represent the two covalent bonds that bind the nitrogen atom to the ketomorphinan.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples describe various aspects of the present invention.

Example 1

Synthesis of Nalbuphone from Noroxymorphone

Noroxymorphone (3.30 g, 11.5 mmol) was combined with 30 mL methanol (MeOH). Approximately 1.93 g (23 mmol)

of cyclobutanecarboxaldehyde (CBCA) was added to the mixture and the slurry was stirred for about 3 hours at room temperature. At that time, a 5 to 2 mixture of 98% formic acid/triethylamine, prepared by adding 98% formic acid (5.34 g, 116 mmol) to triethylamine (4.70 g, 46.4 mmol) in 10 mL of methanol, was added to the slurry. In addition, 9.5 mg of di-μ-chlorobis(ruthenium) (II) dimer was added to the slurry. The reaction was purged by nitrogen gas for 30 minutes and became homogeneous after this time. A steady flow of nitrogen was allowed to pass over the reaction. The reaction was stirred for 24 hours at room temperature. Evaporation of the mixture produced a thick oil, Approximately 10 mL of methanol was added and stirred at room temperature for 1 hour, and a precipitate formed. The precipitate was removed by filtration and washed with 5 mL of cold (5° C.) methanol. The precipitate was dried to yield a product. HPLC analysis indicated that the product contained 0.01% Nalbuphine, 80.0% Nalbuphone (6-ketonalbuphine), and 0.67% noroxymorphone by weight.

Example 2

Synthesis of Nalbuphone from Noroxymorphone with Na$_2$EDTA

Noroxymorphone (3.30 g, 11.5 mmol) was combined with 30 mL methanol (MeOH). Approximately 1.93 g (23 mmol) of cyclobutanecarboxaldehyde (CBCA) was added to the mixture and the slurry was stirred for about 3 hours at room temperature. At that time, a 5 to 2 mixture of 98% formic acid/triethylamine, prepared by adding 98% formic acid (5.34 g, 116 mmol) to triethylamine (4.70 g, 46.4 mmol) in 10 mL of methanol, was added to the slurry. In addition, 9.5 mg of di-μ-chlorobis(ruthenium) (II) dimer followed by 3.76 g of disodium ethylene diamine tetraacetate (Na$_2$EDTA) was added to the slurry. The reaction was purged by nitrogen gas for 30 minutes and became homogeneous after this time. A steady flow of nitrogen was allowed to pass over the reaction. The reaction was stirred for 24 hours at room temperature. Evaporation of the mixture produced a thick oil. Approximately 10 mL of methanol was added and stirred at room temperature for 1 hour, and a precipitate formed. The precipitate was removed by filtration and washed with 5 mL of cold (5° C.) methanol. The precipitate was dried to yield a product. HPLC analysis indicated that the product contained 67.7% nalbuphone and 1.3% noroxymorphone by weight. This process was repeated using slightly less water, yielding a product containing 0.00% Nalbuphine, 78.2% Nalbuphone (6-ketonalbuphine), and 0.82% noroxymorphone by weight.

Example 3

Synthesis of Nalbuphone from Noroxymorphone

Noroxymorphone (3.30 g, 11.5 mmol) was combined with 30 mL methanol (MeOH). Approximately 1.93 g (23 mmol) of cyclobutanecarboxaldehyde (CBCA) was added to the mixture and the slurry was stirred for about 3 hours at room temperature. At that time, a 5 to 2 mixture of 98% formic acid/triethylamine, prepared by adding 98% formic acid (5.34 g, 116 mmol) to triethylamine (4.70 g, 46.4 mmol) in 10 mL of methanol, was added to the slurry. In addition, 9.5 mg of di-μ-chlorobis(ruthenium) (II) dimer was added to the slurry. The reaction was purged by nitrogen gas for 30 minutes and became homogeneous after this time. A steady flow of nitrogen was allowed to pass over the reaction. The reaction was stirred for 24 hours at room temperature. Evaporation of the mixture produced a thick oil. Approximately 10 mL of methanol was added and stirred at room temperature for 1 hour, and a precipitate formed. The precipitate was removed by filtration and washed with 5 mL of cold (5° C.) methanol. The precipitate was dried to yield a product. HPLC analysis indicated that the product contained 0.01% Nalbuphine, 68.1% Nalbuphone (6-ketonalbuphine), and 3.04% noroxymorphone by weight.

Example 4

Synthesis of Nalbuphone from Noroxymorphone with Reduced CBCA and Refluxing of the Solvent Approximately 30 mL methanol (MeOH) was heated to reflux for one hour and then cooled to room temperature. Noroxymorphone (3.30 g, 11.5 mmol) was combined with the methanol. The mixture was heated to reflux for one hour, cooled to room temperature, and then 1.16 g (13.8 mmol) of cyclobutanecarboxaldehyde (CBCA) was added to the mixture and the slurry was stirred for about 3 hours at room temperature. The mixture was heated to reflux for one hour, cooled to room temperature, and then a 5 to 2 mixture of 98% formic acid/triethylamine, prepared by adding 98% formic acid (5.34 g, 116 mmol) to triethylamine (4.70 g, 46.4 mmol) in 10 mL of methanol, was added to the slurry. In addition, 20 mg of di-μ-chlorobis(ruthenium) (II) dimer catalyst was added to the slurry, and the mixture was heated to reflux for one hour and again cooled to room temperature. The reaction was purged by nitrogen gas for 30 minutes and became homogeneous after this time. A steady flow of nitrogen was allowed to pass over the reaction. The reaction was stirred for 24 hours at room temperature. Evaporation of the mixture produced a thick oil. Approximately 10 mL of methanol was added and stirred at room temperature for 1 hour, and a precipitate formed. The precipitate was removed by filtration and washed with 5 mL of cold (5° C.) methanol. The precipitate was dried to yield a product. HPLC analysis indicated that the product contained 0.1% Nalbuphine, 94.8% Nalbuphone (6-ketonalbuphine), and 0.06% noroxymorphone by weight.

Example 5

Synthesis of Nalbuphone from Noroxymorphone with Reduced CBCA, Refluxing of the Solvent, and Ethanolamine Approximately 30 mL methanol (MeOH) was heated to reflux for one hour and then cooled to room temperature. Maintaining this temperature, noroxymorphone (3.30 g, 11.5 mmol) was combined with the methanol. The mixture was heated to reflux for one hour, cooled to room temperature, and then 1.16 g (13.8 mmol) of cyclobutanecarboxaldehyde (CBCA) was added to the mixture and the slurry was stirred for about 3 hours at room temperature. The mixture was heated to reflux for one hour, cooled to room temperature, and then a 5 to 2 mixture of 98% formic acid/triethylamine, prepared by adding 98% formic acid (5.34 g, 116 mmol) to triethylamine (4.70 g, 46.4 mmol) in 10 mL of methanol, was added to the slurry. In addition, 20 mg of di-μ-chlorobis (ruthenium) (II) dimer followed by 20 g of ethanolamine was added to the slurry, and the mixture was heated to reflux for one hour and again cooled to room temperature. The reaction was purged by nitrogen gas for 30 minutes and became homogeneous after this time. A steady flow of nitrogen was allowed to pass over the reaction. The reaction was stirred for 24 hours at room temperature. Evaporation of the mixture produced a thick oil. Approximately 10 mL of methanol was added and stirred at room temperature for 1 hour, and a precipitate formed. The precipitate was removed by filtration and washed with 5 mL of cold (5° C.) methanol. The precipitate was dried to yield a product. HPLC analysis indicated that the product contained 0.2% Nalbuphine, 84.0% Nalbuphone (6-ketonalbuphine), and 0.58% noroxymorphone by weight. This process was repeated except that the ethanolamine was added after the initial stirring of the mixture for three hours at room temperature, yielding a product containing 0.00% Nalbuphine, 87.6% Nalbuphone (6-ketonalbuphine), and 0.0% noroxymorphone by weight. When the procedure was repeated with acetonitrile (ACN) substituted for the MeOH solvent and no refluxing of the solvent, the resulting product contained 0.00% Nalbuphine, 0.00% Nalbuphone (6-ketonalbuphine), and 37.8% noroxymorphone.

Example 6

Naltrexone Base Preparation Using Hydrogen Transfer

Into a round bottom flask was charged noroxymorphone (2.00 g, 0.007 moles), triethylamine (3.52 g, 0.035 mole, 4.85 mL), acetonitrile (15 mL), and cyclopropanecarboxaldehyde (0.98 g, 0.014 mole, 0.92 mL). The mixture was stirred for about 5 minutes at room temperature then >96% formic acid (4.0 g, 0.87 mole, 3.28 mL) was added dropwise. After stirring the mixture for 15 minutes at room temperature, dichloro(p-cymene)Ru(II) dimer (10 mg, 0.000014 moles) was added. The mixture was then stirred at room temperature for about 24 hours. HPLC indicated the reaction was complete. The reaction mixture was evaporated to a thick oil, and distilled water (5.0 mL) was added. The pH was adjusted to 9.4 using 29% $NH_3/H_2O$ where a precipitate formed. The mixture was stirred overnight at room temperature. The precipitate was filtered, washed with distilled water (10 mL), and dried at 90° C. for about 24 hours. The dried precipitate yielded naltrexone base (2.28 g, 95% yield).

Example 7

Naltrexone Base Preparation Using Hydrogen Transfer

Into a round bottom flask was added noroxymorphone (2.19 g, 0.008 mole), cyclopropanecarboxaldehyde (1.07 g, 0.015 mole, 1.00 mL), ammonium formate (2.40 g, 0.038 mole), and isopropanol (20 mL, HPLC grade). After stirring for about 5 minutes, ruthenium (III) chloride (10 mg) was added. The mixture was stirred under nitrogen at room temperature for about 48 hours. HPLC indicated the reaction was complete. To the dark solution, distilled water (1 mL) was added and this mixture stirred for about 18 hours at room temperature. The entire mixture was evaporated under reduced pressure to a thick paste. Distilled water (10 mL) was added and the pH was adjusted to 9.4 from 7.0 using 29% $NH_3/H_2O$ where a precipitate formed. The precipitate was filtered, washed with distilled water (10 mL), and dried overnight at 90° C. The dried precipitate yielded naltrexone base (2.35 g, 91% yield) as an off white solid.

Example 8

N-Benzyloxymorphone Preparation

Into a round bottom flask was added noroxymorphone (6.79 g, 0.024 mole), triethylamine (11.96 g, 0.118 mol, 16.47 mL), acetonitrile (30 mL), and benzaldhehyde (3.76 g, 0.035 mol, 3.93 mL). The mixture was stirred for 5 minutes at room temperature, and then >96% formic acid (13.6 g, 0.295 mole, 11.15 mL) was added drop wise to the mixture. After stirring for 15 minutes at room temperature, dichloro(p-cymene)Ru(II) dimer (72 mg, 0.000118 moles) was added and the resulting mixture was stirred at room temperature for 16 hours. When HPLC indicated that the reaction was complete, the reaction mixture was evaporated to a thick oil, and then distilled water (25 mL) and methanol (5 mL) were added. The pH of the mixture was adjusted to 9.8 by adding 29% $NH_3/H_2O$ drop-wise, forming a precipitate. The mixture was stirred at room temperature for 2 hours, and then the precipitate was filtered, washed with distilled water (25 mL), and dried at 70° C. for 24 h, yielding N-benzyl noroxymorphone (8.30 g, 93% yield).

Example 9

Synthesis of (−)-Naltrexone from (+Noroxymorphone—Reaction 1

The following scheme depicts one reaction for preparing (−)-naltrexone:

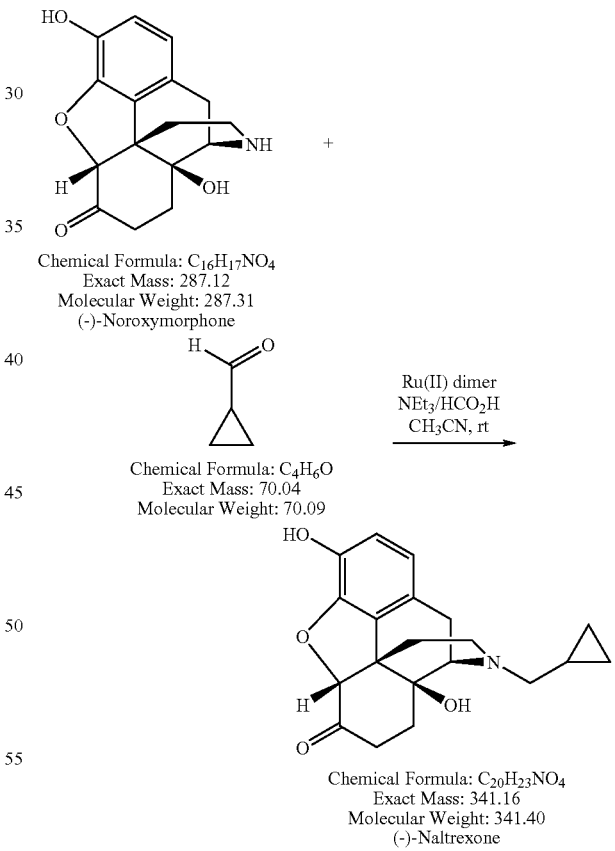

A round bottom flask was charged with noroxymorphone (2.00 g, 0.007 moles), acetonitrile (15 mL), and cyclopropanecarboxaldehyde (0.98 g, 0.014 moles, 0.91 mL). After stirring for a 5 minutes, triethylamine (3.52 g, 0.035 moles, 4.85 mL) was added followed by a drop wise addition of >96% formic acid (4.01 g, 0.087 moles, 3.28 mL). Dichloro(p- cymene)Ru(II) dimer (9 mg, 0.014 mmole) was added. The reaction mixture was stirred at room temperature for 48 h. HPLC analysis indicated the reaction was complete. The reaction mixture was transferred to a round bottom flask and then evaporated under reduced pressure to a thick oil. The thick oil was dissolved in distilled water (5 mL). To this solution was added 29% $NH_3/H_2O$ (~10 mL) until the pH reached 9.4, at which time a precipitate formed. This mixture was stirred for 16 h at room temperature. Then, the product (2.280 g, 0.0067 moles, 95% Yield) was isolated by filtration, washed solid with distilled water (25 mL), and dried in a gravity oven at 90° C. for 24 h.

Example 10

Synthesis of (Naltrexone from (−)-Noroxymorphone—Reaction 2

(−)-Naltrexone was synthesized according to the following reaction scheme:

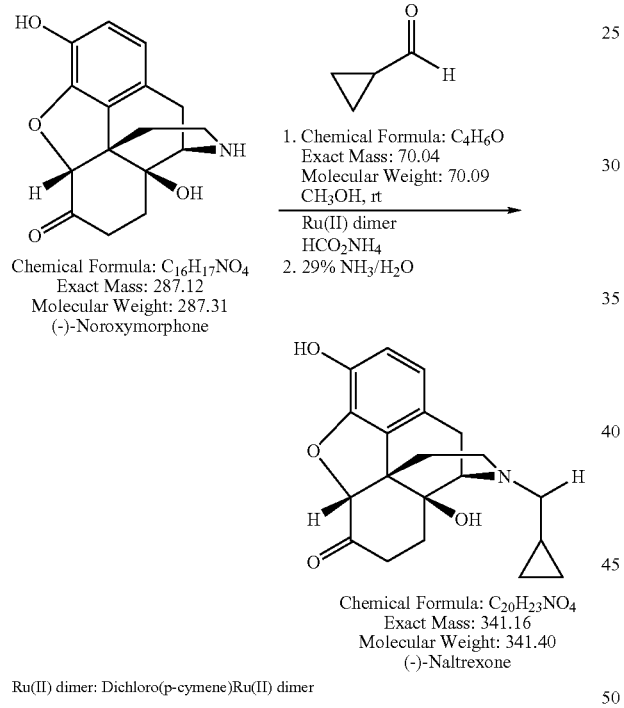

Into a round bottom flask was added, noroxymorphone (2.94 g, 0.01 moles), methanol (20 mL), and cyclopropanecarboxaldehyde (1.43 g, 0.02 moles, 0.91 mL). Ammonium formate (2.58 g, 0.041 moles) was added. Dichloro(p-cymene)Ru(II) dimer (63 mg, 0.10 mmole) was added. The reaction mixture was stirred at room temperature for 24 h. HPLC analysis indicated the reaction was complete. The reaction mixture was transferred to a round bottom flask and then evaporated under reduced pressure leaving a thick oil. To the thick oil was added distilled water (20 mL). To this solution was added 29% $NH_3/H_2O$ (~10 mL) until the pH reached 9.6 and a solid formed. This mixture was stirred for 48 h at room temperature. Then, the product (2.52 g, 0.0074 moles, 72% Yield) was isolated by filtration, washed with distilled water (25 mL), and dried in a gravity oven at 90° C. for 24 h.

Example 11

Synthesis of (−)-Naltrexone from (+Noroxymorphone—Reaction 3

The following reaction scheme depicts another reaction for the synthesis of (−)-naltrexone:

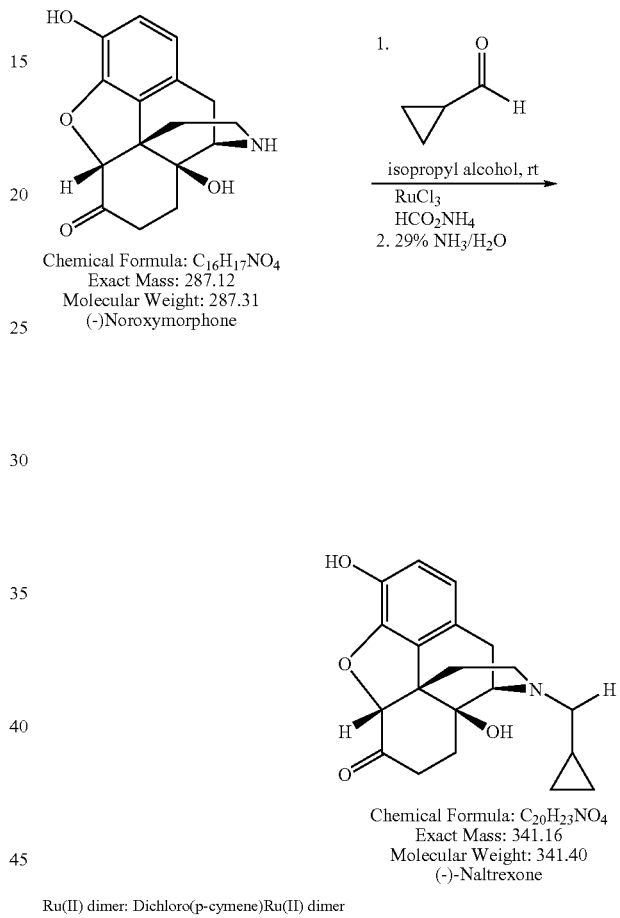

A round bottom flask was charged with noroxymorphone (2.19 g, 0.008 moles), isopropanol (20 mL), and cyclopropanecarboxaldehyde (1.07 g, 0.02 moles, 0.91 mL). Ammonium formate (2.40 g, 0.038 moles) was added. To this solution was added $RuCl_3$ (anhydrous)(10 mg, 0.05 mmole). The reaction mixture was stirred at room temperature for 24 h. HPLC analysis indicated the reaction was complete. To the reaction mixture was added distilled water (1.0 mL) and the mixture was stirred for 16 h at room temperature. Then, the reaction mixture was transferred to a round bottom flask and evaporated under reduced pressure leaving a semi solid. To the semi solid was added distilled water (10 mL). To this solution was added 29% $NH_3/H_2O$ (~5 mL) adjusting the pH from 7.0 to 9.4. A white precipitate formed. The precipitate was filtered, washed with distilled water (10 mL), and dried for 16 h at 95° C. yielding (−)-naltrexone (2.35 g, 0.007 moles, 91% yield) as an off white solid.

Example 12

Synthesis of (−)-N-Benzyloxymorphone from (−)-Noroxymorphone

The following reaction scheme depicts the preparation of (−)-N-benzyloxymorphone:

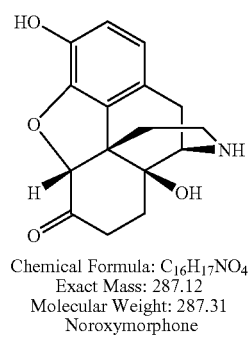

Chemical Formula: $C_{16}H_{17}NO_4$
Exact Mass: 287.12
Molecular Weight: 287.31
Noroxymorphone

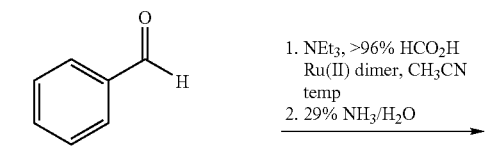

Chemical Formula: $C_7H_6O$
Exact Mass: 106.04
Molecular Weight: 106.12

1. $NEt_3$, >96% $HCO_2H$
   Ru(II) dimer, $CH_3CN$
   temp
2. 29% $NH_3/H_2O$

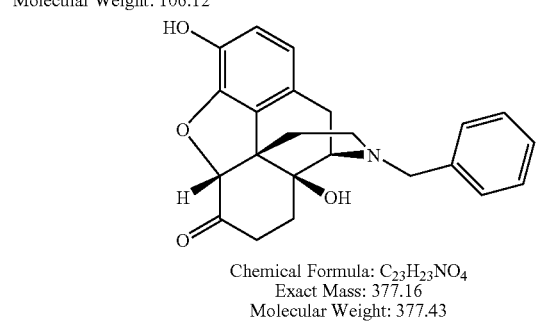

Chemical Formula: $C_{23}H_{23}NO_4$
Exact Mass: 377.16
Molecular Weight: 377.43

Ru(II) dimer = dichloro(p-cymene)Ru(II) dimer

A round bottom flask was charged with noroxymorphone (6.79 g, 0.024 moles), acetonitrile (25 mL), and benzaldehyde (3.76 g, 0.035 moles, 3.93 mL). After stirring for 5 minutes, triethylamine (11.96 g, 0.118 moles, 16.47 mL) was added followed by drop wise addition of >96% formic acid (13.60 g, 0.295 moles, 11.15 mL). Dichloro(p-cymene)Ru(II) dimer (72 mg, 0.12 mmole) was added. The reaction mixture was stirred at room temperature for 16 h, When HPLC analysis indicated the reaction was complete, the reaction mixture was filtered through a glass-fritted funnel containing celite (~1.0 g), and the funnel was rinsed with acetonitrile (20 mL). The filtrate was transferred into a round bottom flask and the solvent was removed under reduced pressure leaving a thick oil. The thick oil was dissolved in distilled water (25 mL) and methanol (5.0 mL). To this solution was added 29% $NH_3/H_2O$ (~25 mL) until the pH reached 9.8 and a solid formed. This mixture was stirred at room temperature for 2 h. Then, the product (8.30 g, 0.022 moles, 93% Yield) was isolated by filtration, washed with a mixture of distilled water (25 mL) and methanol (5 mL), and dried in a vacuum oven for 24 h.

Example 13

Synthesis of (+)-Naltrexone from (+)-Noroxymorphone (+)-Naltrexone was synthesized according to the following reaction scheme:

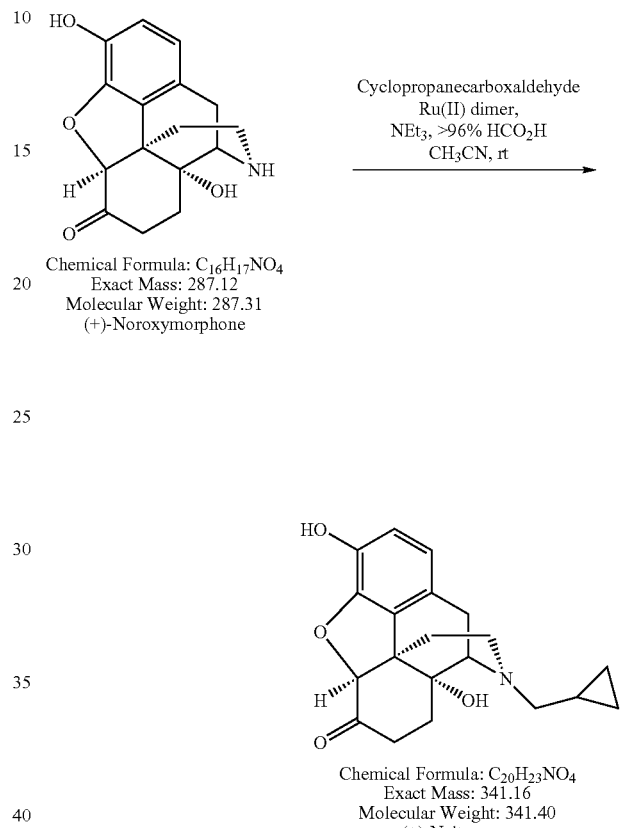

Into a round bottom flask was added, (+)-noroxymorphone (1.73 g, 0.006 moles), acetonitrile (15 mL), and cyclopropanecarboxaldehyde (0.63 g, 0.009 moles, 0.67 mL). After stirring for 5 minutes, triethylamine (3.05 g, 0.030 moles, 4.20 mL) was added followed by drop wise addition of >96% formic acid (3.46 g, 0.075 moles, 2.84 mL). Dichloro(p-cymene)Ru(II) dimer (18 mg, 0.03 mmole) was added. The reaction mixture was stirred at room temperature for 72 h. HPLC analysis indicated the reaction was complete. The reaction mixture was transferred to a round bottom flask and the solvent was removed under reduced pressure leaving a thick oil. The thick oil was dissolved in distilled water (10 mL). To this solution was added 29% $NH_3/H_2O$ (~5 mL) until the pH reached 9.6 and a solid formed. The solid (1.21 g, 0.0035 moles) was isolated by filtration, washed with distilled water (10 mL), and dried in a gravity oven at 75° C. for 48 h. The filtrate was extracted using ethyl acetate (3×25 mL), the extracts were combined, dried over anhydrous $MgSO_4$, and then evaporated. A second yield of (+)-naltrexone (0.80 g, 0.0023 moles) was isolated by column chromatography (Silica Gel G60, 70-230 mesh ASTM) eluting with 80% ethyl acetate heptane. Combined yield of (+)-naltrexone obtained by both isolations was 2.01 g, 0.0059 moles, 97% yield, as an off white solid.

What is claimed is:

1. A process for the preparation of a N-alkylated ketomorphinan compound of Formula (IV):

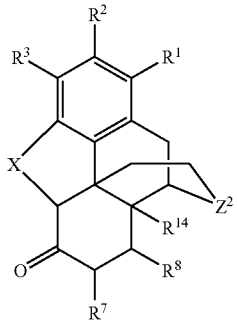

the process comprising:
maintaining a ketone group of a N-imine ketomorphinan or hemiaminal ketomorphinan as unprotected; and, reducing the N-imine ketomorphinan or hemiaminal ketomorphinan in the presence of a hydrogen source and a catalyst without substantially reducing the 6-keto functionality to an alcohol, the N-imine ketomorphinan or hemiaminal ketomorphinan compound of Formula (III):

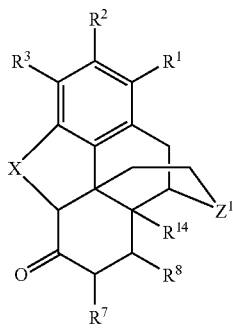

wherein:
$R^1$, and $R^2$ are independently selected from the group consisting of hydrogen, hydrocarbyl, substituted hydrocarbyl, halo, and $\{-\}OR^{15}$;
$R^3$, $R^7$, and $R^8$ are independently selected from the group consisting of hydrogen, hydrocarbyl, substituted hydrocarbyl, and $\{-\}OR^{15}$;
$R^9$ is selected from the group consisting of hydrogen, acyl, hydrocarbyl, substituted hydrocarbyl, and heterocyclo;
$R^{14}$ is selected from the group consisting of hydrogen and hydroxy;
$R^{15}$ is selected from the group consisting of hydrogen, hydrocarbyl, substituted hydrocarbyl, and a hydroxy protecting group;
X is oxygen;
$Z^1$ is selected from the group consisting of $\{-\}NCH(OH)(R^9)$, and $\{-\}N^+=CH(R^9)$; and
$Z^2$ is $\{-\}NCH_2R^9$.

2. The process of claim 1, wherein the N-imine ketomorphinan or hemiaminal ketomorphinan is formed by reacting an aldehyde comprising the formula $R^9CHO$ with a 6-ketonormorphinan compound of the following structure:

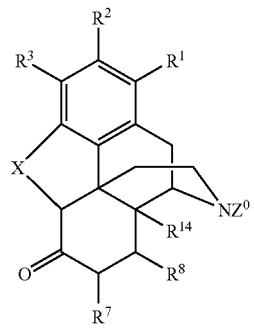

wherein:
$R^1$, and $R^2$ are independently selected from the group consisting of hydrogen, hydrocarbyl, substituted hydrocarbyl, halo, and $\{-\}OR^{15}$;
$R^3$, $R^7$, and $R^8$ are independently selected from the group consisting of hydrogen, hydrocarbyl, substituted hydrocarbyl, and $\{-\}OR^{15}$;
$R^9$ is selected from the group consisting of hydrogen, acyl, hydrocarbyl, substituted hydrocarbyl, and heterocyclo;
$R^{14}$ is selected from the group consisting of hydrogen and hydroxy;
$R^{15}$ is selected from the group consisting of hydrogen, hydrocarbyl, substituted hydrocarbyl, and a hydroxy protecting group;
$Z^0$ is selected from the group consisting of hydrogen; and
X is oxygen.

3. The process of claim 2, wherein the aldehyde is selected from the group consisting of formaldehyde, acetaldehyde, cyclopropanecarboxaldehyde, cyclobutanecarboxaldehyde, benzaldehyde, substituted benzaldehyde, and a combination thereof; the 6-ketonormorphinan is selected from the group consisting of noroxymorphone, noroxycodone, norhydrocodone, northebaine, nororipavine, and norhydromorphone; and the N-alkylated ketomorphinan compound of Formula (IV) is selected from the group consisting of nalbuphone, naltrexone, naloxone, and a combination thereof.

4. The process of claim 3, wherein the amount of aldehyde is from about 1.0 to about 3.0 equivalents per equivalent of the 6-ketonormorphinan; and the reaction of the aldehyde and the 6-ketonormorphinan occurs within a temperature range from about 20° C. to about 60° C. and in the presence of a solvent system comprising an organic solvent.

5. The process of claim 4, wherein the organic solvent is selected from the group consisting of methanol, ethanol, isopropanol, n-propanol, n-butanol, acetonitrile, tetrahydrofuran, ethyl ether, dimethylformamide, dimethylacetamide, N-methylpyrrolidinone, dimethylsulfoxide, ethyl acetate, propyl acetate, and a combination thereof.

6. The process of claim 1, wherein the ketone functionality within the ketomorphinan is reduced less than about 5%.

7. The process of claim 1, wherein the hydrogen source comprises a protic compound selected from the group consisting of formic acid, organic or inorganic salts of formic acid, isopropanol, n-propanol, n-butanol, and a combination thereof; and the catalyst comprises ruthenium, rhodium, or iridium.

8. The process of claim 1, wherein the hydrogen source is formic acid; and the catalyst is selected from the group consisting of dichloro(arene)Ru(II) dimer, dichloro(pentamethylcyclopentadienyl)Rh(II) dimer, BINAP-Ru (II) diacetate, BINAP-Ru (II) dichloride, BINAP-Ru (II) dibromide, BINAP-Ru (II) diiodide, [RuCI((R or S)BINAP)($C_6H_6$)]Cl, dichloro(pentamethylcyclopentadienyl)iridium (III) dimer, Ru(III) chloride, $RuCl_3$hydrate, Ru(III) acetylacetonate, tetraalkylammonium $RuCl_4$, and pyridinium $RuCl_4$.

9. The process of claim 1, wherein the optical activity of the N-alkylated ketomorphinan compound of Formula (IV) is selected from the group consisting of (+), (−), and a combination thereof; and the configuration of the chiral carbons C-5, C-13, C-14, and C-9 of the N-alkylated ketomorphinan compound of Formula (IV) may be selected from the group consisting of RRRR, RRSR, RRRS, RRSS, RSRR, RSSR, RSRS, RSSS, SRRR, SRSR, SRRS, SRSS, SSRR, SSSR, SSRS, and SSSS; provided, however, that the C-15 and the C-16 carbons are both either on the alpha face of the molecule or the beta face of the molecule.

10. The process of claim 1, wherein the N-imine or hemiaminal ketomorphinan compound of Formula (III) is an analog of noroxymorphone; the catalyst comprises a di- μ-chlorobis (ruthenium)(II) dimer; and, the hydrogen source comprises formic acid or a formic acid salt.

11. The process of claim 10, further comprising producing the ketomorphinan of Formula (IV) in greater than 85% yield.

* * * * *